United States Patent
Qu et al.

(10) Patent No.: US 10,526,873 B2
(45) Date of Patent: Jan. 7, 2020

(54) TAGGED CORROSION INHIBITORS FOR USE IN SUBTERRANEAN OPERATIONS

(71) Applicant: Multi-Chem Group, LLC, San Angelo, TX (US)

(72) Inventors: Liangwei Qu, The Woodlands, TX (US); Nathan Darrell Davis, Conroe, TX (US)

(73) Assignee: Multi-Chem Group, LLC, Houston, TX (US)

(*) Notice: Subject to any disclaimer, the term of this patent is extended or adjusted under 35 U.S.C. 154(b) by 333 days.

(21) Appl. No.: 15/302,001

(22) PCT Filed: May 16, 2014

(86) PCT No.: PCT/US2014/038382
§ 371 (c)(1),
(2) Date: Oct. 5, 2016

(87) PCT Pub. No.: WO2015/174995
PCT Pub. Date: Nov. 19, 2015

(65) Prior Publication Data
US 2017/0122078 A1 May 4, 2017

(51) Int. Cl.
*E21B 41/02* (2006.01)
*C09K 8/54* (2006.01)
(Continued)

(52) U.S. Cl.
CPC .............. *E21B 41/02* (2013.01); *C09K 8/54* (2013.01); *E21B 47/1015* (2013.01);
(Continued)

(58) Field of Classification Search
CPC ...... E21B 41/02; E21B 49/08; E21B 47/1015; E21B 2049/085; G01V 8/10; C09K 8/54; C09K 2208/32
See application file for complete search history.

(56) References Cited

U.S. PATENT DOCUMENTS 2,851,426 A * 9/1958 Hughes ................ C07D 417/06
206/524.4
2,875,210 A * 2/1959 Bollenback .......... C07D 233/14
252/394

(Continued)

FOREIGN PATENT DOCUMENTS

EP 0526251 A1 2/1993
WO 2009/064719 A1 5/2009
(Continued)

OTHER PUBLICATIONS

Schlumberger Oilfield Glossary entries for "casing", "tubing joint", and "tubing hanger", accessed Oct. 9, 2018 via www.glossary.oilfield.slb.com.*

(Continued)

*Primary Examiner* — Blake E Michener
(74) *Attorney, Agent, or Firm* — Tenley Krueger; Baker Botts L.L.P.

(57) ABSTRACT

Compositions, treatment fluids, and methods for providing corrosion inhibition in subterranean operations, pipelines, and other related operations are provided. In one embodiment, the methods comprise providing a tagged corrosion-inhibiting additive that comprises an imidazoline-based compound bonded with a detectable moiety; and introducing the tagged corrosion-inhibiting additive into at least a portion of a subterranean formation or pipeline.

20 Claims, 5 Drawing Sheets

(51) Int. Cl.
  *E21B 49/08*  (2006.01)
  *G01V 8/10*  (2006.01)
  *E21B 47/10*  (2012.01)
  *E21B 43/25*  (2006.01)
  *G01N 21/73*  (2006.01)

(52) U.S. Cl.
  CPC .............. *E21B 49/08* (2013.01); *G01V 8/10* (2013.01); *C09K 2208/32* (2013.01); *E21B 43/25* (2013.01); *E21B 2049/085* (2013.01); *G01N 21/73* (2013.01)

(56) References Cited

U.S. PATENT DOCUMENTS

| | | | | |
|---|---|---|---|---|
| 3,262,791 A * | 7/1966 | Dickson | ............ | B01D 19/0413 106/14.13 |
| 3,265,512 A * | 8/1966 | Dickson | ............ | B01D 19/0413 106/14.13 |
| 3,488,294 A * | 1/1970 | Annand | ................ | A01N 25/30 210/735 |
| 3,514,251 A * | 5/1970 | Redmore | ............ | B01D 17/047 252/390 |
| 3,553,101 A * | 1/1971 | Zisis | ................ | C23F 11/04 203/7 |
| 3,654,993 A * | 4/1972 | Smith | ................ | C09K 8/54 166/279 |
| 3,687,847 A * | 8/1972 | Maddox et al. | ........ | C09K 8/54 252/392 |
| 3,779,935 A * | 12/1973 | McDougall | ............ | C11D 1/62 252/390 |
| 4,964,468 A * | 10/1990 | Adams | ................ | C09K 8/54 166/310 |
| 5,152,177 A * | 10/1992 | Buck | ................ | E21B 41/02 166/250.05 |
| 5,236,036 A * | 8/1993 | Ungemach | ............ | E21B 17/20 138/139 |
| 5,322,630 A * | 6/1994 | Williams | ................ | C09K 8/54 507/241 |
| 5,322,640 A | 6/1994 | Byrne et al. | | |
| 5,393,464 A * | 2/1995 | Martin | ................ | C09K 8/54 252/389.23 |
| 5,590,716 A * | 1/1997 | Mansfield | ................ | C09K 8/54 166/267 |
| 5,939,362 A * | 8/1999 | Johnson | ................ | C09K 8/54 252/390 |
| 6,303,079 B1 * | 10/2001 | Meyer | ................ | C07D 233/18 106/14.12 |
| 6,395,225 B1 | 5/2002 | Pou et al. | | |
| 7,057,050 B2 * | 6/2006 | Meyer | ................ | C07D 233/06 252/394 |
| 7,682,526 B2 * | 3/2010 | Culley | ................ | C07D 233/06 252/387 |
| 8,551,925 B2 * | 10/2013 | Nguyen | ................ | C23F 11/10 507/243 |
| 8,585,930 B2 * | 11/2013 | Tiwari | ................ | C07D 213/04 252/392 |
| 9,534,300 B2 * | 1/2017 | Gill | ................ | C23F 11/149 |
| 2001/0023614 A1 * | 9/2001 | Tubel | ................ | E21B 23/03 73/152.39 |
| 2002/0109080 A1 * | 8/2002 | Tubel | ................ | E21B 23/03 250/227.14 |
| 2003/0013893 A1 * | 1/2003 | Meyer | ................ | C09K 8/54 548/566 |
| 2004/0135125 A1 | 7/2004 | Morris et al. | | |
| 2005/0181380 A1 | 8/2005 | Isobe | | |
| 2006/0180794 A1 * | 8/2006 | Goddard | ................ | C07C 211/10 252/387 |
| 2007/0267193 A1 | 11/2007 | Hills et al. | | |
| 2010/0105580 A1 * | 4/2010 | Becker | ................ | C08F 20/04 507/225 |
| 2011/0071056 A1 | 3/2011 | Saini et al. | | |
| 2011/0071059 A1 | 3/2011 | Nguyen et al. | | |
| 2012/0032093 A1 | 2/2012 | Moore et al. | | |
| 2012/0048808 A1 | 3/2012 | Zhou et al. | | |
| 2012/0270758 A1 | 10/2012 | Saini et al. | | |
| 2013/0234063 A1 * | 9/2013 | Moore | ................ | C02F 5/12 252/180 |
| 2015/0198038 A1 * | 7/2015 | Bartetzko | ................ | E21B 49/00 166/250.05 |
| 2016/0046854 A1 * | 2/2016 | Gordon | ................ | C09K 8/42 166/250.12 |
| 2016/0265316 A1 * | 9/2016 | Reyes | ................ | E21B 41/02 |
| 2016/0333484 A1 * | 11/2016 | Gulabani | ................ | C07D 233/10 |
| 2017/0002629 A1 * | 1/2017 | Hurtevent | ................ | C09K 8/528 |
| 2017/0009130 A1 * | 1/2017 | Wadekar | ................ | C09K 8/035 |
| 2017/0306504 A1 * | 10/2017 | Moloney | ................ | C23F 11/10 |
| 2018/0172596 A1 * | 6/2018 | Hurtevent | ................ | G01N 21/643 |

FOREIGN PATENT DOCUMENTS

WO  2009/088702 A1  7/2009
WO  2010/128322 A1  11/2010

OTHER PUBLICATIONS

International Search Report and Written Opinion issued in related PCT Application No. PCT/US2014/038382 dated Feb. 24, 2015, 11 pages.

Tyagi, Rashmi, V. K. Tyagi, and S. K. Pandey. "Imidazoline and its derivatives: an overview." Journal of oleo science 56.5 (2007): 211-222.

Brondel, Denis, et al. "Corrosion in the oil industry." Oilfield review 6.2 (1994): 4-18.

Escalante, Jaime, Manuel Carrillo-Morales, and Irma Linzaga. "Michael additions of amines to methyl acrylates promoted by microwave irradiation." Molecules 13.2 (2008): 340-347.

International Preliminary Report on Patentability issued in related Application No. PCT/US2014/038382, dated Dec. 1, 2016 (7 pages).

Frullano, L., et al, "Towards Targeted MRI: New MRI Contrast Agents for Sialic Acid Detection", Chemistry, vol. 10, No. 20, Oct. 11, 2004, pp. 5205-5217.

Extended European Search Report issued in related European Application No. 14892126.5, dated Nov. 16, 2017, 7 pages.

\* cited by examiner

TAGGED CORROSION INHIBITORS FOR USE IN SUBTERRANEAN OPERATIONS

CROSS-REFERENCE TO RELATED APPLICATION

The present application is a U.S. National Stage Application of International Application No. PCT/US2014/038382 filed May 16, 2014, which is incorporated herein by reference in its entirety for all purposes.

BACKGROUND

The present disclosure relates to compositions, treatment fluids, and methods for providing corrosion inhibition in subterranean operations, pipelines, and other related operations.

The corrosion of metal surfaces occurs when the metal surfaces are contacted by a corrosive environment containing an oxidizer (e.g., an electrochemical oxidizer, a chemical oxidizer or the like). Illustrative corrosive environments include, for example, acidic environments, environments containing water vapor in the presence of air and/or oxygen, and environments containing chloride or bromide ions, carbon dioxide and/or hydrogen sulfide. As used herein, the term "corrosion" refers to any reaction between a material and its environment that causes some deterioration of the material or its properties. Examples of common types of corrosion include, but are not limited to, the rusting of a metal, the dissolution of a metal in acids, and patina development on the surface of a metal.

Acidic environments can be produced by acidic treatment fluids that are commonly used in a number of operations in the oil and chemical industries. In such operations, any metal surfaces present are subjected to the corrosive environment of the treatment fluid. For example, metal surfaces (e.g., piping, tubular goods, heat exchangers and reactors) can be exposed to acidic treatment fluids in industrial chemical equipment. In subterranean applications, metal surfaces on various types of equipment are often exposed to corrosive conditions during downhole operations. For example, acidic treatment fluids are frequently utilized in the treatment of subterranean formations, and additional corrosive components including brine, carbon dioxide and/or hydrogen sulfide are commonly encountered downhole. Pipelines and conduits used to transport fluids between various locations (in the oilfield industry and elsewhere) also may be exposed to acidic fluids that can cause corrosion.

Acidic treatment fluids for downhole use include, for example, acidic clean-up fluids and stimulation fluids. Acidic stimulation fluids include, for example, treatment fluids used in hydraulic fracturing or matrix acidizing treatments. Acidic treatment fluids can include a variety of acids such as, for example, hydrochloric acid, formic acid, hydrofluoric acid, and the like.

While acidic treatment fluids are useful for a variety of downhole operations, they can be somewhat problematic due to potential metal surface corrosion on downhole production tubing and tools, for which the repair or replacement costs are high. Furthermore, under typical downhole conditions, corrosion rates of metal surfaces are frequently increased due to elevated temperatures and pressures that are present in the subterranean environment. In addition to damage caused to downhole metal surfaces, corrosion can result in significant quantities of the acidic treatment fluid being neutralized, thereby reducing the treatment fluid's downhole effectiveness.

To combat potential corrosion problems, certain corrosion inhibitors have been used to reduce or substantially prevent corrosion of metal and metal alloy surface on downhole equipment, all with varying levels of success. As used herein, the term "inhibit" and its derivatives refer to a lessening of the tendency of a phenomenon to occur and/or the degree to which that phenomenon occurs. The term "inhibit" does not imply any particular degree or amount of inhibition. Corrosion inhibitor compositions frequently include imidazoline as a corrosion inhibiting component. However, these corrosion inhibitors are not always effective, for example, if they are not placed in the desired locations and/or are not delivered to the desired locations at sufficiently high concentrations.

BRIEF DESCRIPTION OF THE FIGURES

These drawings illustrate certain aspects of some of the embodiments of the present disclosure, and should not be used to limit or define the disclosure.

Figure 1:
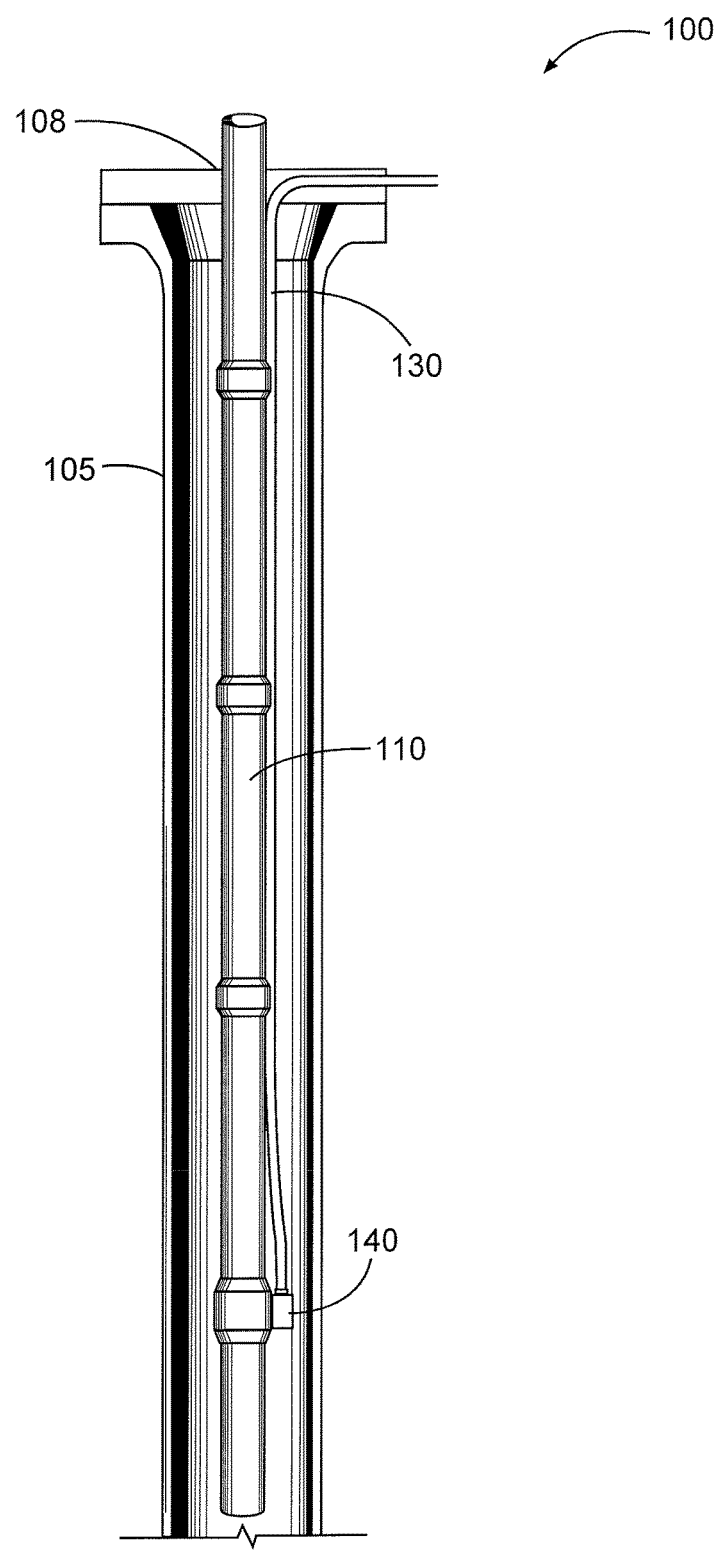
FIG. 1 is a diagram illustrating an injection system that may be used in accordance with certain embodiments of the present disclosure.
Figure 2A:
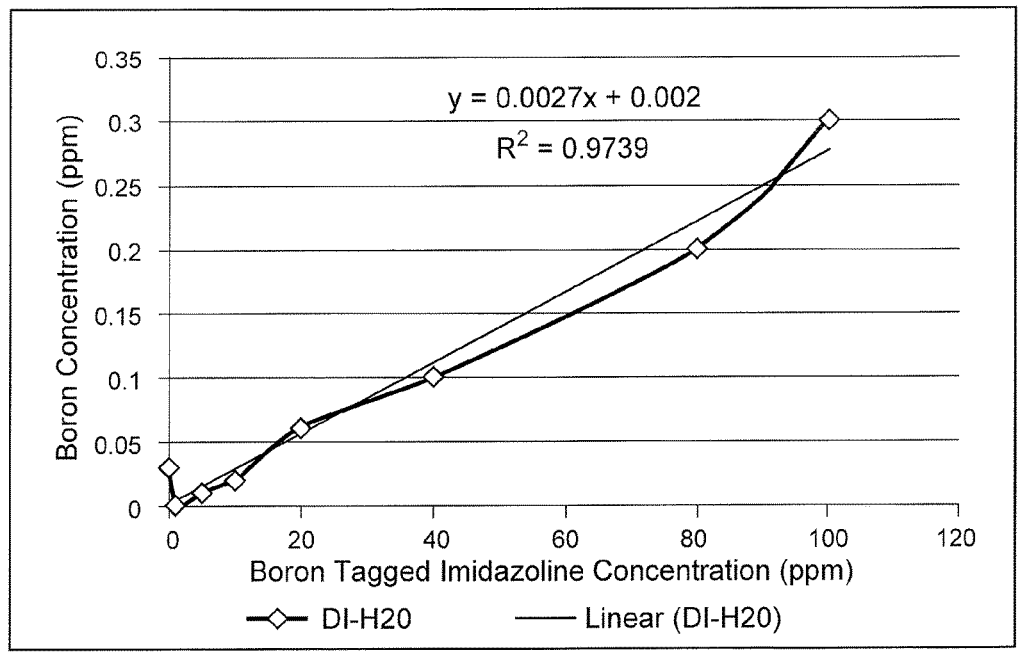
FIGS. 2A, 2B, 2C, and 2D are graphs illustrating data relating to concentrations of tagged corrosion-inhibiting additives of the present disclosure detected in various fluid samples according to one embodiment of the present disclosure.
Figure 2B:
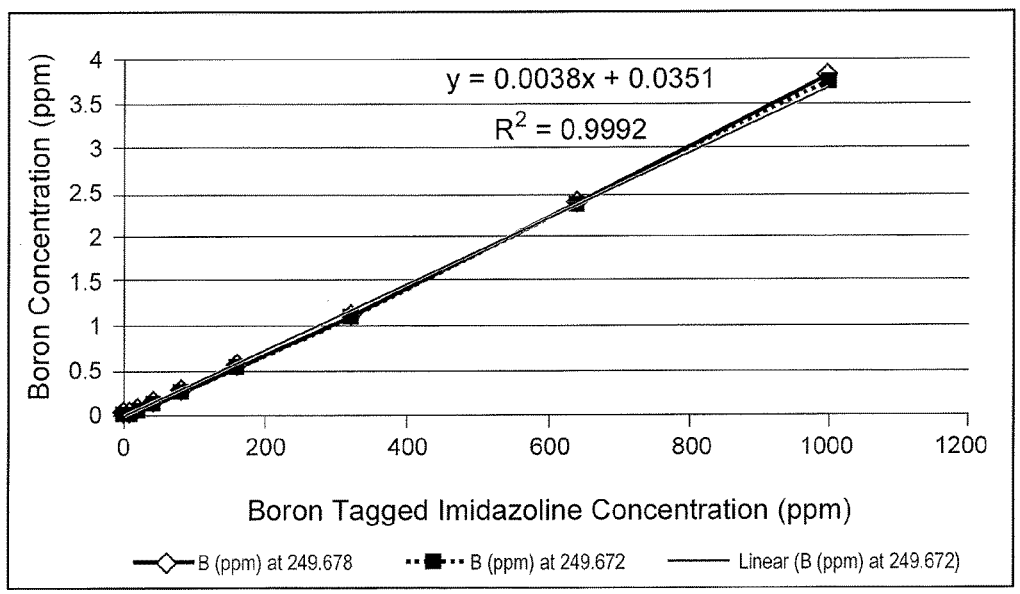
Figure 2C:
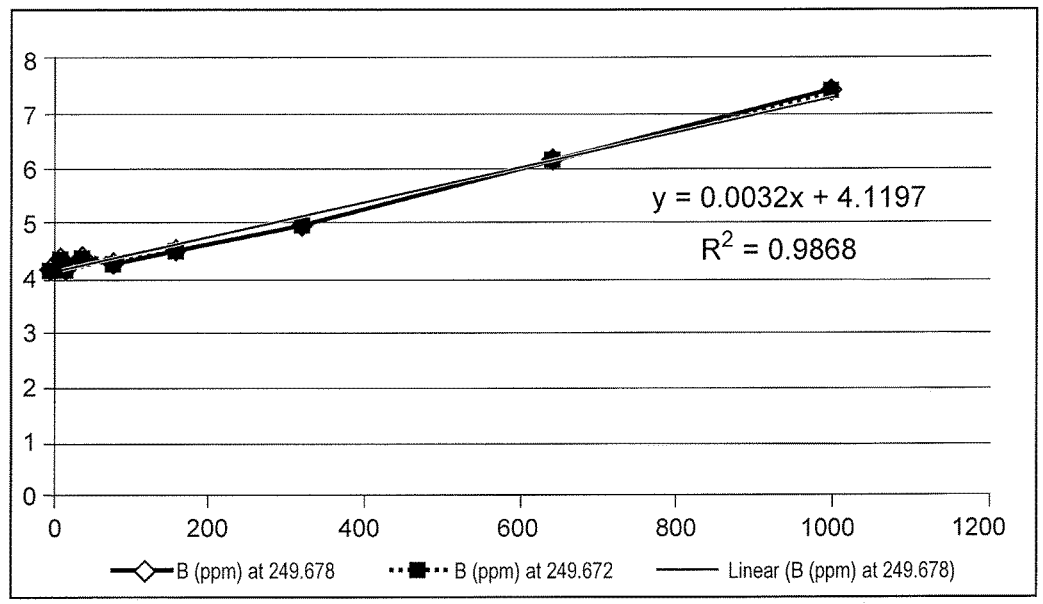
Figure 2D:
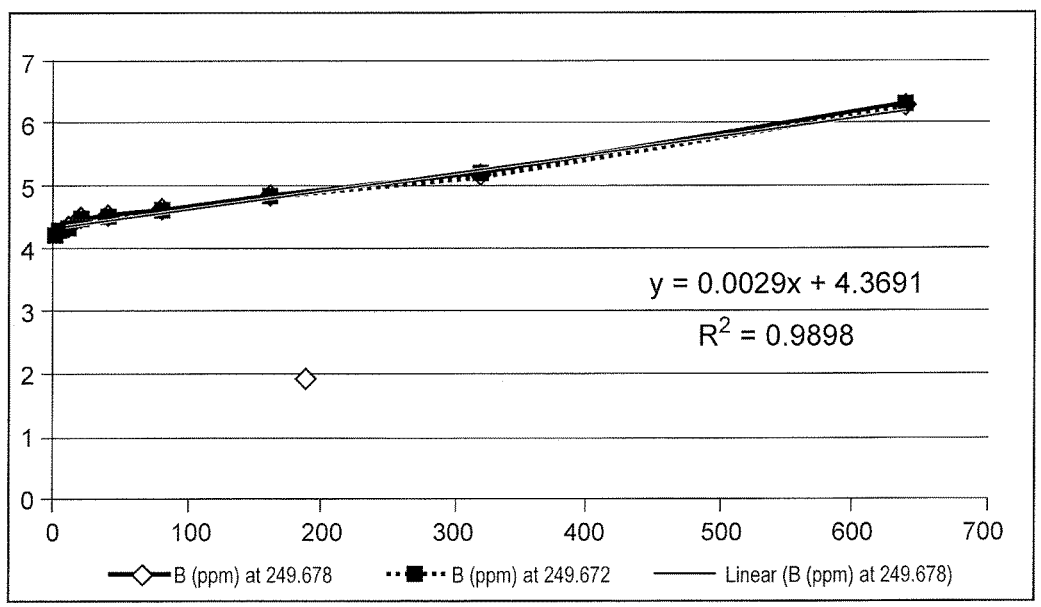

While embodiments of this disclosure have been depicted and described and are defined by reference to example embodiments of the disclosure, such references do not imply a limitation on the disclosure, and no such limitation is to be inferred. The subject matter disclosed is capable of considerable modification, alteration, and equivalents in form and function, as will occur to those skilled in the pertinent art and having the benefit of this disclosure. The depicted and described embodiments of this disclosure are examples only, and not exhaustive of the scope of the disclosure.

DETAILED DESCRIPTION

Illustrative embodiments of the present disclosure are described in detail herein. In the interest of clarity, not all features of an actual implementation may be described in this specification. It will of course be appreciated that in the development of any such actual embodiment, numerous implementation-specific decisions may be made to achieve the specific implementation goals, which may vary from one implementation to another. Moreover, it will be appreciated that such a development effort might be complex and time-consuming, but would nevertheless be a routine undertaking for those of ordinary skill in the art having the benefit of the present disclosure.

The present disclosure relates to compositions, treatment fluids, and methods for providing corrosion inhibition in subterranean operations, pipelines, and other related operations. Specifically, the methods and compositions of the present disclosure generally involve the synthesis and use of corrosion inhibiting additives that are tagged with one or more detectable moieties (i.e., a detectable element or functional group) so that they may be traced for residual concentrations using various analytical methods when placed in those locations. The tagged corrosion inhibiting additives of the present disclosure generally comprise an imidazoline-based compound bonded with a detectable element or functional group. In the methods of the present disclosure, a corrosion inhibiting additive of the present disclosure may be placed in a subterranean formation, well bore, pipeline, or other location where a corrosive environment or conditions are present. The residual amount and/or concentration of the tagged corrosion inhibiting additive in a specific location then may be determined by analyzing fluid samples from that location (e.g., the well bore or pipeline) and determining the concentration of the detectable element or functional group.

The methods, compositions, and additives of the present disclosure may, among other benefits, provide a monitoring tool for establishing effective treatment rates for corrosion inhibitors where conventional tools such as corrosion coupons or inline probes cannot be used, and may do so more accurately, reliably, and efficiently even where such conventional methods are available. In certain embodiments, the enhanced monitoring techniques enabled by the methods, compositions, and additives of the present disclosure may lead to decreased failure rates due to inadequate treatment, and/or may reduce cost incurred by overtreatment to avoid failures. The methods, compositions, and additives of the present disclosure also may reduce operator cost by eliminating the need for time-consuming monitoring methods and lost time and resources due to inaccurate monitoring. The methods, compositions and additives of the present disclosure also may decrease the uncertainty of corrosion inhibitor transport in certain applications involving pipelines, liquid-producing wells, annulus drip applications, capillary strings, umbilical lines, batch treatments, gas lift applications, and the like.

The imidazoline-based compounds used in the methods and compositions of the present disclosure may comprise any compound including the following functional group or structure:

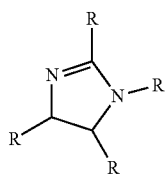

wherein the R groups may be hydrogen atoms or carbon-based functional groups such as alkanes, alkenes, amines, and the like having any number of carbon atoms. Each of the R groups in a given imidazoline-based compound according to the formula above may comprise the same R group or may comprise different types of R groups and/or have different numbers of carbon atoms. The compound may include one or more imidazoline derivatives, such as bisimidazoline, quaternized imidazolinium salts, and the like. The imidazoline-based compound may be provided as a reagent, or may be generated in the synthesis process, for example, by the reaction of one or more amines or amides.

The detectable elements and functional groups used in the methods and compositions of the present disclosure may comprise any element or functional group that is not generally found in subterranean formations or produced water, or is only present in low concentrations. Examples of detectable elements that may be used include, but are not limited to, boron, phosphorus, bromine, iodine, selenium, and combinations thereof. In certain embodiments, the detectable element may be provided as a component of another compound or reagent to be reacted with the imidazoline-based compound or its precursors. For example, boron may be provided in one or more borates, such as boric acid, borax, and the like.

The tagged corrosion inhibiting additives of the present disclosure may be synthesized by any means known in the art. Examples of two synthesis schemes that may be used to synthesize tagged corrosion inhibiting additives are illustrated in Schemes 1 and 2 below.

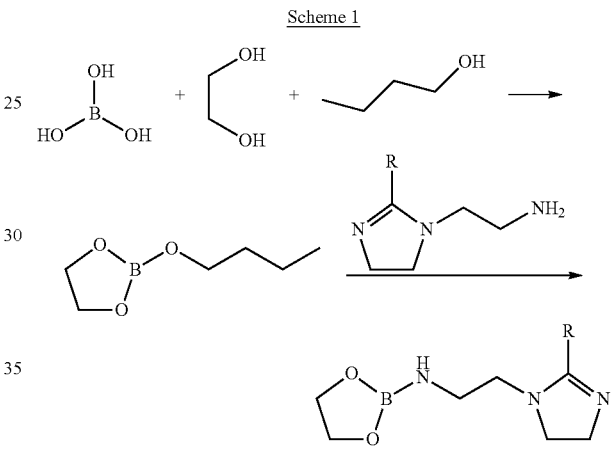

Scheme 1

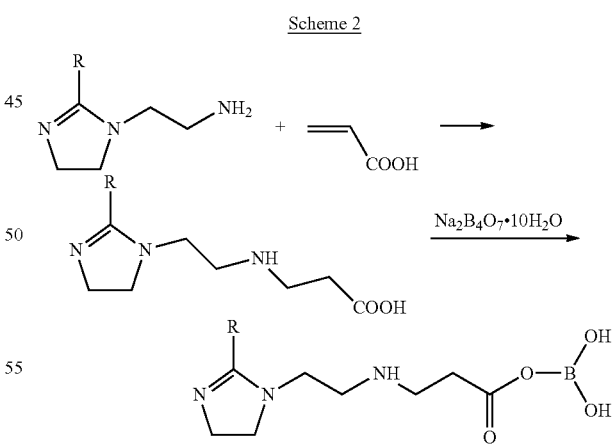

Scheme 2

In Scheme 1, boric acid reacts with butanol in an ethylene glycol solvent to provide a cyclic borate intermediate that is substituted onto an imidazoline-based amine. In Scheme 2, a fatty acid is substituted onto an imidazoline-based amine, and then a borate is substituted onto the fatty acid chain. In another embodiment, a detectable element such as boron may be substituted onto a fatty acid chain, which then may be reacted with a noncyclic amine (e.g., diethylenetriamine (DETA) to form imidazoline molecules tagged with boron. In certain embodiments, a synthesis scheme as described above may yield a concentration of active imidazoline molecules of about 76%. The ratio of the various reagents (e.g., amines, fatty acids, reagents containing the detectable element, etc.) may be varied to produce tagged compounds having different structures and/or to produce a higher or lower yield of tagged imidazoline-based compounds. A person of skill in the art, with the benefit of this disclosure, will recognize how to vary those amounts to produce the desired tagged compounds and structures.

The molar concentration or amount of the imidazoline-based compound used in the methods and compositions of the present disclosure may be similar to those used in conventional uses of these compounds as corrosion inhibitors, although the amount or concentration of the imidazoline-based compound by mass, once tagged with the detectable element, may be higher than the amounts of untagged imidazoline used conventionally. In certain embodiments, the corrosion inhibiting additives of the present disclosure may be introduced into a fluid in a concentration of from about 10 parts per million ("ppm") to about 300 ppm. In certain embodiments, the corrosion inhibiting additives of the present disclosure may be introduced into a solution or fluid (e.g., a fluid in a pipeline) in a concentration of from about 60 ppm to about 80 ppm. In certain embodiments, a tagged corrosion inhibiting additive of the present disclosure may be used in combination with one or more additional corrosion inhibiting additives, including but not limited to additives that are not tagged with a detectable element or functional group.

The corrosion inhibiting additives of the present disclosure may be introduced in a subterranean formation and/or well bore in conjunction with one or more treatment fluids. Such treatment fluids may comprise any treatment fluid known in the art (e.g., treatment fluids suitable for use in subterranean formations). As used herein, the term "treatment fluid" refers to any fluid that may be used in an application in conjunction with a desired function and/or for a desired purpose. The term "treatment" does not imply any particular action by the fluid or any component thereof. The treatment fluids of the present disclosure generally comprise a base fluid and, in certain embodiments, comprise one or more acids. Examples of common treatment fluids include, but are not limited to, drilling fluids, spacer fluids, completion fluids, and work-over fluids. Treatment fluids of the present disclosure optionally may comprise any number of additional additives in combination with the catechol component and amine component. Other examples of such additional additives include, but are not limited to, weighting agents, surfactants, emulsifiers, acids, fluorides, fluid loss control additives, gas, nitrogen, carbon dioxide, surface modifying agents, tackifying agents, foamers, additional corrosion inhibitors, scale inhibitors, catalysts, clay control agents, biocides, friction reducers, antifoam agents, bridging agents, dispersants, flocculants, additional $H_2S$ scavengers, $CO_2$ scavengers, oxygen scavengers, lubricants, viscosifiers, breakers, relative permeability modifiers, resins, particulate materials (e.g., proppant particulates), wetting agents, coating enhancement agents, filter cake removal agents, and the like. A person skilled in the art, with the benefit of this disclosure, will recognize the types of additives that may be included in the fluids of the present disclosure for a particular application.

The methods and compositions of the present disclosure may be used during or in conjunction with any subterranean operation. Suitable subterranean operations may include, but are not limited to, preflush treatments, afterflush treatments, drilling operations, hydraulic fracturing treatments, sand control treatments (e.g., gravel packing), acidizing treatments (e.g., matrix acidizing or fracture acidizing), "frac-pack" treatments, well bore clean-out treatments, and other operations where a treatment fluid or corrosion-inhibiting additive of the present disclosure may be useful. In certain embodiments, the methods and/or compositions of the present disclosure may be used in near well bore clean-out operations, wherein a treatment fluid of the present disclosure may be circulated in the subterranean formation, thereby suspending or solubilizing particulates residing in the formation. The treatment fluid then may be recovered out of the formation, carrying the suspended or solubilized particulates with it. In certain embodiments, a tagged corrosion inhibitor of the present disclosure may be pumped into a portion of a subterranean formation (e.g., a fracture) where the fluid may leak off into the formation faces near the well bore, forming a reservoir of corrosion inhibitor near the well bore. When fluids (e.g., hydrocarbons) are produced back out of the well bore, the corrosion inhibitor may slowly feed into the oil being produced. In certain embodiments, the methods and/or compositions of the present disclosure may be used in construction and/or operation of pipelines (e.g., transportation pipelines, distribution pipelines, etc.) or umbilical equipment that may be used, among other purposes, to transport various fluids (e.g., treatment fluids and/or fluids produced from subterranean formations).

The corrosion inhibiting additives of the present disclosure may be introduced into any subterranean formation, well bore penetrating a subterranean formation, tubular, and/or pipeline using any method or equipment known in the art. Introduction of the corrosion inhibiting additives of the present disclosure may in such embodiments include delivery via any of a tube, umbilical, pump, and combinations thereof. A corrosion inhibiting additives of the present disclosure may, in various embodiments, be delivered downhole (e.g., into the wellbore) or into top-side flowlines or pipelines. For example, these additives may be applied to a subterranean formation and/or well bore using batch treatments, squeeze treatments, continuous treatments, and/or combinations thereof. In certain embodiments, a batch treatment may be performed in a subterranean formation by stopping production from the well and pumping a specific amount or quantity of the corrosion inhibiting additive into a well bore at one point in time, which may be repeated at one or more points in time during the life of a well. In other embodiments, a squeeze treatment may be performed by dissolving the corrosion inhibiting additive in a suitable solvent at a suitable concentration and squeezing that solvent carrying the additive downhole into the formation, allowing production out of the formation to bring the corrosion inhibiting additive to its desired location. In still other embodiments, a corrosion inhibiting additive of the present disclosure may be injected into a portion of a subterranean formation using an annular space or capillary injection system to continuously introduce the additive into the formation. Other means and/or equipment that may be used to continuously inject corrosion inhibiting additives of the present disclosure into a well bore include, but are not limited to slip-stream systems, annulus drip systems, umbilical strings, gas lift systems, continuous metering systems, subsurface hydraulic systems, bypass feeders, and the like. In certain embodiments, such continuous injection equipment at a well site may be controlled from a remote location and/or may be partially or completely automated. In certain embodiments, a treatment fluid comprising a corrosion inhibiting additive of the present disclosure may be circulated in the well bore using the same types of pumping systems and equipment at the surface that are used to introduce treatment fluids or additives into a well bore penetrating at least a portion of the subterranean formation. In certain embodiments, a corrosion inhibiting additive of the present disclosure could be dried and formed into a solid for delivery into rat holes, tanks, and/or a wellbore.

For example, a corrosion inhibiting additive of the present disclosure may be introduced into a well bore using a capillary injection system as shown in FIG. 1. Referring now to FIG. 1, well bore 105 has been drilled to penetrate a portion of a subterranean formation 100. A tubing 110 (e.g., production tubing) has been placed in the well bore 105. A capillary injection tube 130 is disposed in the annular space between the outer surface of tubing 110 and the inner wall of well bore 105. The capillary injection tube 130 is connected to a side-pocket mandrel 140 at a lower section of the tubing 110. A corrosion inhibiting additive may be injected into capillary injection tube 130 at the wellhead 108 at the surface such that it mixes with production fluid at or near the side-pocket mandrel 140. As the production fluid flows through the tubing 110, the corrosion inhibiting additive may treat the inner surface of the tubing 110. Other capillary injection systems and side pocket mandrel devices (e.g., those used in gas lift production) may be used in a similar manner to the system shown in FIG. 1.

In certain embodiments, a corrosion inhibiting additive of the present disclosure may be added to a pipeline where one or more fluids enter the pipeline and/or at one or more other locations along the length of the pipeline. In these embodiments, the corrosion inhibiting additive may be added in batches or injected substantially continuously while the pipeline is being used. In certain embodiments, a batch treatment may be performed in at least a portion of a pipeline by introducing a specific amount or quantity of the corrosion inhibiting additive into a pipeline at one point in time, which may be repeated at one or more points in time during the life of a pipeline.

Once introduced into a treatment fluid, subterranean formation, well bore, pipeline, or other location, the tagged corrosion inhibiting additives of the present disclosure may be detected or traced in fluid samples taken from any location where the corrosion inhibiting additive is believed to be. For example, where the tagged corrosion inhibiting additive is introduced into a subterranean formation or well bore, fluid samples may be taken at the surface (e.g., at a well head) and/or one or more downhole locations. Where tagged corrosion inhibiting additive is introduced into a pipeline, fluid samples may be taken at one or more locations along the pipeline. The fluid samples may be analyzed using any technique known in the art for detecting the detectable element or functional group (e.g., standard water analysis techniques), which may be conducted at the site where the samples were taken or at an offsite location. Examples of analysis techniques that may be suitable in certain embodiments of the present disclosure include, but are not limited to, inductively coupled plasma optical emission spectrometry (ICP-OES) or inductively coupled plasma atomic emission spectroscopy (ICP-AES), liquid or gas chromatography (e.g., HPLC), mass spectroscopy, or any combination thereof.

The data generated in this analysis may be used determine the presence and/or concentration of a tagged corrosion inhibiting additive of the present disclosure. That data may be used to determine, among other things, whether an obstruction may be preventing fluid and corrosion inhibiting additive from flowing to the sampled location, and/or whether additional corrosion inhibiting additives should be added (e.g., if the concentration of the tagged corrosion-inhibiting additive is less than a predetermined effective amount necessary to sufficiently inhibit corrosion). Where a tagged corrosion inhibiting additive of the present disclosure is applied in a batch treatment, the data generated in this analysis may be used to determine a residual concentration of the corrosion inhibiting additive after a certain period of time has passed since the last batch treatment. In certain embodiments, this data also may be used to infer the presence and/or location of additional additives (e.g., corrosion inhibiting additives) that are not tagged with a detectable element or functional group that were mixed and/or injected with a tagged corrosion inhibiting additive of the present disclosure. In certain embodiments, an operator or user may use some or all of this data to assess whether the inhibitors are being applied in a particular operation in sufficient concentrations and/or sufficiently frequently (e.g., where batch treatments are used) to provide the desired level of corrosion inhibition. Based at least in part on this data, an operator or user may select or adjust the concentration of a corrosion-inhibiting additive to use, for example, in an ongoing continuous treatment and/or in a subsequent batch treatment. Based at least in part on this data, an operator or user also may select and/or adjust the frequency and/or timing for a subsequent batch treatment of a corrosion-inhibiting additive. In certain embodiments, such subsequent treatments may use a tagged corrosion-inhibiting additive of the present disclosure and/or any other corrosion-inhibiting additive known in the art.

In certain embodiments, the data generated in this analysis may be stored electronically and/or loaded into a database (e.g., an online database accessible from remote locations) for access by operators and/or technicians who may use that data to assess various conditions and treatment plans. One example of such a database where this data may be loaded and accessed is the MVP 2.0™ database available from Multi-Chem, a division of Halliburton Energy Services.

To facilitate a better understanding of the present disclosure, the following examples of certain aspects of preferred embodiments are given. The following examples are not the only examples that could be given according to the present disclosure and are not intended to limit the scope of the disclosure or claims.

Examples

Synthesis and Detection of Boron-Tagged Corrosion Inhibitor

A tagged corrosion inhibiting additive of the present disclosure was prepared according to Scheme 1 above by adding about 50 g ethylene glycol and 20 g of n-butanol to a 250-mL, four-neck, round bottom flask equipped with a thermometer, and a Dean-Stark adaptor equipped with a reflux condenser. About 15.5 g boric acid was added to the flask and heated under reflux with mechanical agitation until approximately 12.7 g of water was collected. The reaction mixture was cooled to room temperature and 92.6 g imidazoline was slowly added. The reaction mixture was then heated at 150° C. until substantially all of the n-butanol was removed. The reaction mixture was cooled to room temperature, and a viscous liquid was formed.

The presence of boron-tagged reaction product was confirmed using NMR, which demonstrated a downward chemical shift (as compared to the NMR spectrum of boric acid)

from 20 ppm to 23 ppm for the reaction intermediate and an upward chemical shift from 23 ppm to 10 ppm in the boron-tagged product.

Four sets of standards spiked with the boron-tagged imidazoline were analyzed to investigate minimum detection amounts and linear response in deionized water and seawater samples. The synthesized product was formulated to 20% activity by weight, and was added to samples of deionized water and synthetic seawater in varying concentrations as listed in Tables 1-4 below. The synthetic seawater was prepared according to ASTM-D-1141-98 using a salt mixture that contains a baseline boron concentration of 4.7 ppm, as reported by the manufacturer. As shown in Tables 3 and 4, the boron concentrations detected were shifted by expected amounts. The synthetic seawater standards described in Table 4 further included 2-3 drops of nitric acid ($HNO_3$) per 100 mL sample, which is a commonly-used technique to preserve samples for ICP-OES analysis to reduce the chance for precipitation of various salt and hydroxide species. As noted in Tables 2-4, ICP-OES measurements were taken in the analysis of certain standards at two different wavelengths (249.678 nm and 249.672 nm).

TABLE 1

Standard in deionized water

| Imidazoline conc (ppm) | Boron detected (ppm) |
|---|---|
| 0 | 0.03 |
| 1 | 0 |
| 5 | 0.01 |
| 10 | 0.02 |
| 20 | 0.06 |
| 40 | 0.1 |
| 80 | 0.2 |
| 100 | 0.3 |

TABLE 2

Standards in deionized water

| Imidazoline conc (ppm) | Boron detected (ppm) @ 249.678 nm | Boron detected (ppm) @ 249.672 nm |
|---|---|---|
| 0 | 0 | 0 |
| 10 | 0.03 | 0.03 |
| 20 | 0.06 | 0.06 |
| 40 | 0.13 | 0.13 |
| 80 | 0.25 | 0.25 |
| 160 | 0.53 | 0.53 |
| 320 | 1.1 | 1.1 |
| 640 | 2.35 | 2.35 |
| 1000 | 3.8 | 3.76 |

TABLE 3

Standards in synthetic seawater

| Imidazoline conc (ppm) | Boron detected (ppm) @ 249.678 nm | Boron detected (ppm) @ 249.672 nm |
|---|---|---|
| 0 | 4.14 | 4.11 |
| 10 | 4.34 | 4.32 |
| 20 | 4.18 | 4.15 |
| 40 | 4.39 | 4.36 |
| 80 | 4.29 | 4.26 |
| 160 | 4.49 | 4.49 |
| 320 | 4.95 | 4.96 |
| 640 | 6.13 | 6.13 |
| 1000 | 7.42 | 7.43 |

TABLE 4

Standards in synthetic seawater (acidized with $HNO_3$)

| Imidazoline conc (ppm) | Boron detected (ppm) @ 249.678 nm | Boron detected (ppm) @ 249.672 nm |
|---|---|---|
| 0 (without $HNO_3$) | 4.26 | 4.25 |
| 0 | 4.24 | 4.21 |
| 1 | 4.33 | 4.3 |
| 5 | 4.3 | 4.27 |
| 10 | 4.34 | 4.33 |
| 20 | 4.49 | 4.49 |
| 40 | 4.52 | 4.51 |
| 80 | 4.62 | 4.62 |
| 160 | 4.84 | 4.84 |
| 320 | 5.17 | 5.2 |
| 640 | 6.27 | 5.3 |

The data from Tables 1-4 is plotted and curve-fit in FIGS. 2A through 2D. As shown in those figures, the concentrations of boron detected in the standards using ICP-OES demonstrated near-linear relationships with the concentrations of boron-tagged imidazoline added to those standards, with $R^2$ values ranging from 0.9739 to 0.9992.

Performance/Corrosion Inhibition

Figure 3:
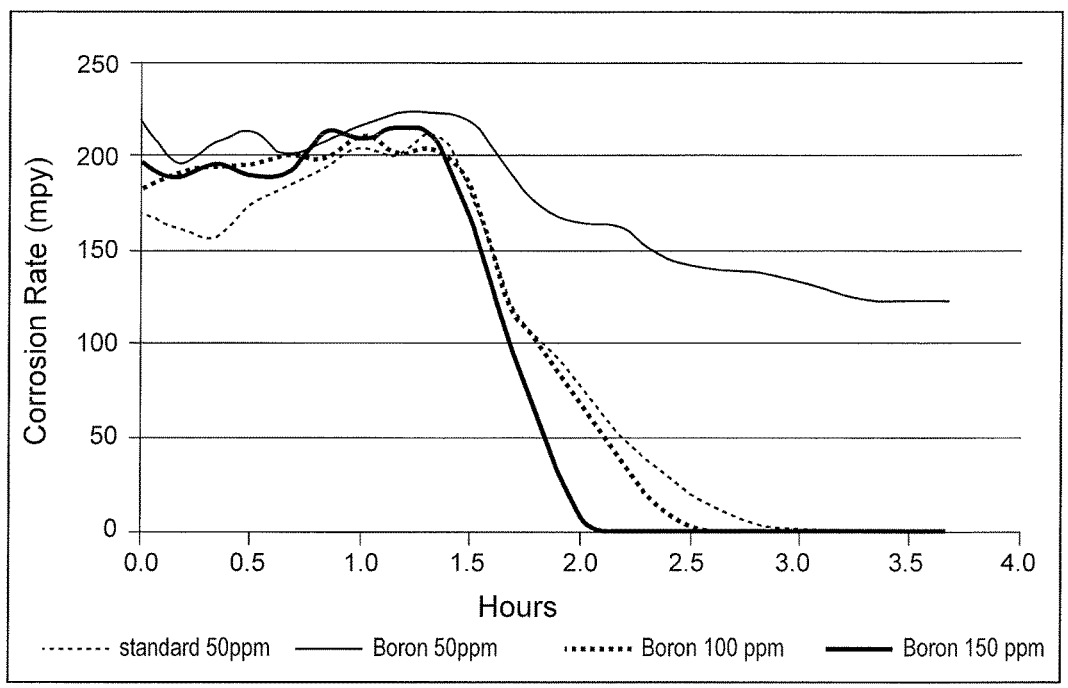
FIG. 3 is a graph illustrating data relating to corrosion rates using conventional corrosion-inhibiting additives and tagged corrosion-inhibiting additives of the present disclosure at various concentrations.
Figure 3A:
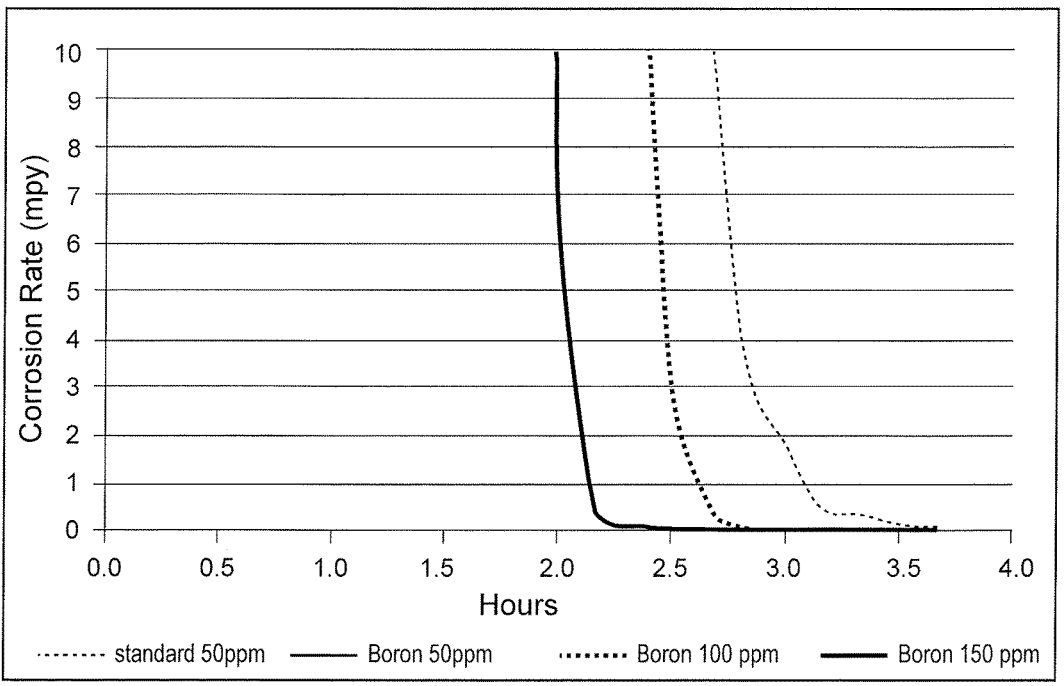
FIG. 3A is a graph showing a certain portion of the graph from FIG. 3 at a different scale.

The corrosion inhibiting action of a boron-tagged imidazoline additive of the present disclosure was evaluated against that of a standard imidazoline corrosion inhibitor. The standard and tagged corrosion inhibitors were formulated at 20% activity by weight, and added in various concentrations (50 ppm of the standard inhibitor; 50 ppm, 100 ppm, and 150 ppm of the boron-tagged inhibitor) to test solutions comprising 800 mL synthetic seawater and 80 mL LVT-200 light petroleum distillate (available from various suppliers). The test solutions were heated to 150° F., continuously purged with $CO_2$, and stirred with a magnetic stir bar/plate combination. The corrosion inhibitors were added after approximately 1.5 hours. Corrosion rate measurements were made using a linear polarization resistance technique and a Gamry electrochemical measurement system. The working electrode (1018 carbon steel) was polarized +/−15 mV from its free corroding potential at a scan rate of 0.4 mV/sec. The results from the first set of tests are shown in FIGS. 3 and 3A. These data demonstrate that a boron-tagged imidazoline additive of the present disclosure may inhibit corrosion in certain environments, although in this case was not as effective in inhibiting corrosion as the standard imidazoline corrosion inhibitor at a treatment rate of 50 ppm. However, a distinct increase in performance was observed at treatment rates of 100 ppm and 150 ppm.

Figure 4:
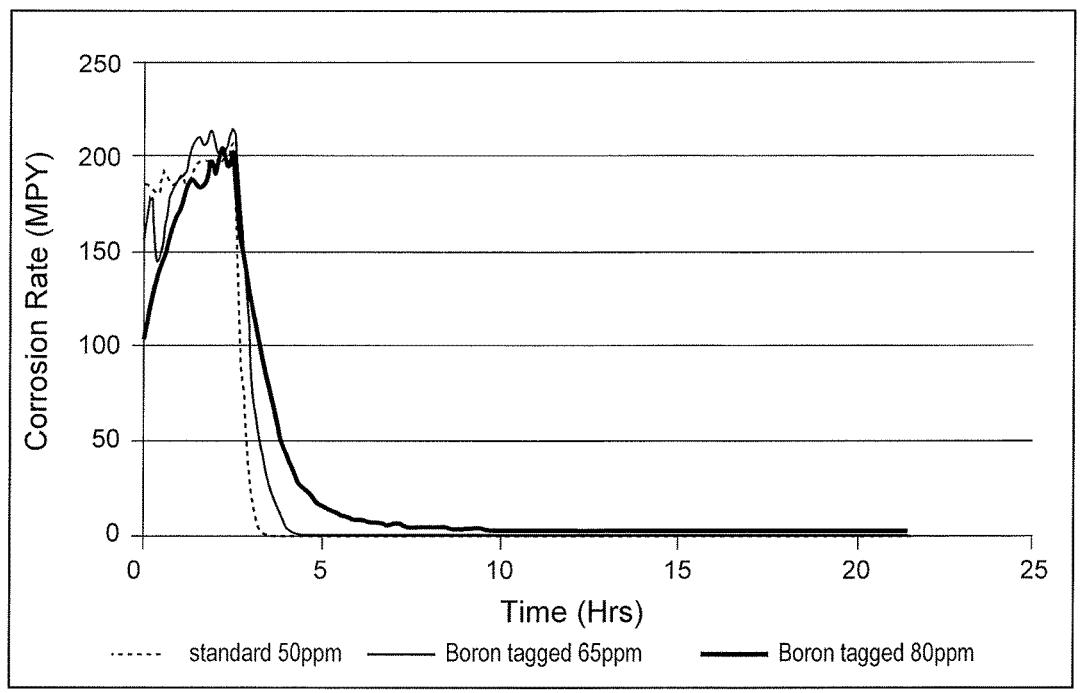
FIG. 4 is a graph illustrating data relating to corrosion rates using conventional corrosion-inhibiting additives and tagged corrosion-inhibiting additives of the present disclosure at various concentrations.
Figure 4A:
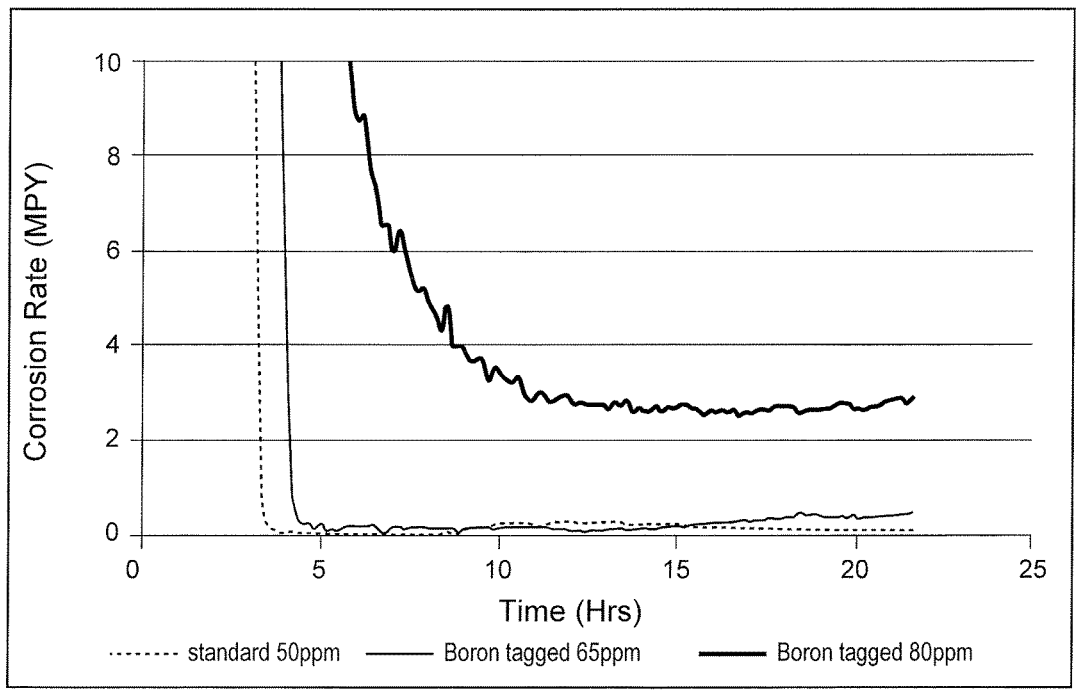
FIG. 4A is a graph showing a certain portion of the graph from FIG. 4 at a different scale.

The tests described above were repeated (except that the corrosion inhibitors were added after approximately 2.8 hours) using the boron-tagged inhibitor at concentrations of 65 ppm and 80 ppm, the results of which are shown in FIGS. 4 and 4A. These data demonstrate that a boron-tagged imidazoline additive of the present disclosure may inhibit corrosion in certain environments, and in this case performed similarly at 65 ppm to the standard imidazoline corrosion inhibitor at 50 ppm. This difference in performance may be explained by the actual activity of the standard additive (100%) as compared to the boron-tagged additive (~64%), which may be a function of (a) the increase in the molecular weight of the boron-tagged imidazoline due to the addition of the ethylene glycol and borate adducts, and/or (b) dilution of the boron-tagged additive in unreacted ethylene glycol.

An embodiment of the present disclosure is a method comprising: providing a tagged corrosion-inhibiting additive that comprises an imidazoline-based compound bonded with a detectable moiety; and introducing the tagged corrosion-inhibiting additive into at least a portion of a subterranean formation.

Another embodiment of the present disclosure is a method comprising: providing a tagged corrosion-inhibiting additive that comprises an imidazoline-based compound bonded with a detectable moiety; and introducing the tagged corrosion-inhibiting additive into at least a portion of a pipeline carrying one or more fluids from one location along the pipeline to another location along the pipeline.

Another embodiment of the present disclosure is a corrosion-inhibiting composition comprising an imidazoline-based compound bonded with a detectable moiety that comprises boron.

Another embodiment of the present disclosure is a method comprising: providing a tagged corrosion-inhibiting additive that comprises an imidazoline-based compound bonded with a detectable moiety; introducing an amount of the tagged corrosion-inhibiting additive into a tubular at a first time; taking a sample of fluid from at least a portion of the tubular after the quantity of the tagged corrosion-inhibiting additive was introduced; analyzing the fluid sample to determine a concentration of the tagged corrosion-inhibiting additive in the fluid sample; and introducing an amount of an additional corrosion-inhibiting additive into the tubular at a second time, wherein the second time was selected based at least in part on the concentration of the tagged corrosion-inhibiting additive in the fluid sample.

Therefore, the present disclosure is well adapted to attain the ends and advantages mentioned as well as those that are inherent therein. The particular embodiments disclosed above are illustrative only, as the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered or modified and all such variations are considered within the scope and spirit of the present disclosure. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an", as used in the claims, are defined herein to mean one or more than one of the element that it introduces. If there is any conflict in the usages of a word or term in this specification and one or more patent or other documents that may be incorporated herein by reference, the definitions that are consistent with this specification should be adopted.

What is claimed is:

1. A method comprising:
providing a tagged corrosion-inhibiting additive that comprises an imidazoline-based compound covalently bonded with a detectable moiety through a synthesis scheme selected from the group consisting of:
(i) a first synthesis scheme comprising:
reacting an acid comprising the detectable moiety with an alcohol in a solvent to form a cyclic intermediate that comprises the detectable moiety, and
substituting the cyclic intermediate with the imidazoline-based compound such that the imidazoline-based compound is covalently bonded with a detectable moiety; and
(ii) a second synthesis scheme comprising:
substituting a fatty acid onto the imidazoline-based compound, and
substituting the detectable moiety onto the fatty acid; and
introducing the tagged corrosion-inhibiting additive into at least a portion of a subterranean formation.

2. The method of claim 1 further comprising:
taking a sample of fluid from at least a portion of the subterranean formation; and
analyzing the sample of fluid to determine a concentration of the tagged corrosion-inhibiting additive in the fluid.

3. The method of claim 2 wherein an inductively coupled plasma optical emission spectrometry technique is used to analyze the fluid sample.

4. The method of claim 2 wherein:
the concentration of the tagged corrosion-inhibiting additive in the fluid sample is less than a predetermined effective amount; and
the method further comprises introducing an additional corrosion-inhibiting additive into at least a portion of the subterranean formation.

5. The method of claim 4 wherein the additional corrosion-inhibiting additive comprises an additional tagged corrosion-inhibiting additive.

6. The method of claim 1 wherein a well bore penetrates the portion of the subterranean formation, and at least a portion of tubing resides in the well bore.

7. The method of claim 1 wherein introducing the tagged corrosion-inhibiting additive into at least a portion of the subterranean formation comprises injecting the tagged corrosion-inhibiting additive into a capillary injection tube disposed in a well bore that penetrates at least a portion of the subterranean formation.

8. The method of claim 1 wherein introducing the tagged corrosion-inhibiting additive into at least a portion of the subterranean formation comprises:
introducing a first amount of the tagged corrosion-inhibiting additive into a well bore penetrating at least a portion of the subterranean formation at a first time; and
introducing a second amount of the tagged corrosion-inhibiting additive into the well bore at a second time.

9. The method of claim 8 wherein the method further comprises:
taking a sample of fluid from at least a portion of the subterranean formation after the first amount of the tagged corrosion-inhibiting additive was introduced;
analyzing the fluid sample to determine a concentration of the tagged corrosion-inhibiting additive in the fluid sample,
and wherein the second time was selected based at least in part on the concentration of the tagged corrosion-inhibiting additive in the fluid sample.

10. The method of claim 1 wherein the detectable moiety comprises at least one element selected from the group consisting of: boron, phosphorus, bromine, iodine, selenium, and any combination thereof.

11. A method comprising:
providing a tagged corrosion-inhibiting additive that comprises an imidazoline-based compound covalently bonded with a detectable moiety through a synthesis scheme selected from the group consisting of:
(i) a first synthesis scheme comprising:
reacting an acid comprising the detectable moiety with an alcohol in a solvent to form a cyclic intermediate that comprises the detectable moiety, and
substituting the cyclic intermediate with the imidazoline-based compound such that the imidazoline-based compound is covalently bonded with a detectable moiety; and
(ii) a second synthesis scheme comprising:
substituting a fatty acid onto the imidazoline-based compound, and
substituting the detectable moiety onto the fatty acid; and
introducing the tagged corrosion-inhibiting additive into at least a portion of a pipeline carrying one or more fluids from one location along the pipeline to another location along the pipeline.

12. The method of claim 11 further comprising:
taking a sample of fluid from at least a portion of the pipeline; and
analyzing the sample of fluid to determine a concentration of the tagged corrosion-inhibiting additive in the fluid.

13. The method of claim 12 wherein an inductively coupled plasma optical emission spectrometry technique is used to analyze the fluid sample.

14. The method of claim 12 wherein:
the concentration of the tagged corrosion-inhibiting additive in the fluid sample is less than a predetermined effective amount; and
the method further comprises introducing an additional corrosion-inhibiting additive into at least a portion of the pipeline.

15. The method of claim 14 wherein the additional corrosion-inhibiting additive comprises an additional tagged corrosion-inhibiting additive.

16. The method of claim 11 wherein introducing the tagged corrosion-inhibiting additive into at least a portion of the pipeline comprises:
introducing a first amount of the tagged corrosion-inhibiting additive into the pipeline at a first time; and
introducing a second amount of the tagged corrosion-inhibiting additive into the pipeline at a second time.

17. The method of claim 16 wherein the method further comprises:
taking a sample of fluid from at least a portion of the pipeline after the first amount of the tagged corrosion-inhibiting additive was introduced;
analyzing the fluid sample to determine a concentration of the tagged corrosion-inhibiting additive in the fluid sample,
and wherein the second time was selected based at least in part on the concentration of the tagged corrosion-inhibiting additive in the fluid sample.

18. The method of claim 11 wherein the detectable moiety comprises at least one element selected from the group consisting of: boron, phosphorus, bromine, iodine, selenium, and any combination thereof.

19. A corrosion-inhibiting composition comprising an imidazoline-based compound covalently bonded with a detectable moiety that comprises boron through a synthesis scheme selected from the group consisting of:
(i) a first synthesis scheme comprising:
reacting an acid comprising the detectable moiety with an alcohol in a solvent to form a cyclic intermediate that comprises the detectable moiety, and
substituting the cyclic intermediate with the imidazoline-based compound such that the imidazoline-based compound is covalently bonded with a detectable moiety; and
(ii) a second synthesis scheme comprising:
substituting a fatty acid onto the imidazoline-based compound, and
substituting the detectable moiety onto the fatty acid.

20. The corrosion-inhibiting composition of claim 19 wherein the imidazoline-based compound comprises an imidazoline-based amine.

* * * * *